United States Patent
Sageser et al.

(10) Patent No.: US 7,047,608 B2
(45) Date of Patent: May 23, 2006

(54) METHOD OF PRODUCING A SHAPED TAMPON

(75) Inventors: David Mark Sageser, Cincinnati, OH (US); Francis Michael Nicholas, Addlestone (GB); Charles John Berg, Jr., Wyoming, OH (US); James Henry Barton, Oberems (DE)

(73) Assignee: The Procter & Gamble Company, Cincinnati, OH (US)

( * ) Notice: Subject to any disclaimer, the term of this patent is extended or adjusted under 35 U.S.C. 154(b) by 132 days.

(21) Appl. No.: 10/150,049

(22) Filed: May 16, 2002

(65) Prior Publication Data

US 2003/0172504 A1    Sep. 18, 2003

Related U.S. Application Data

(60) Provisional application No. 60/365,669, filed on Mar. 18, 2002.

(51) Int. Cl.
*A61F 13/20* (2006.01)

(52) U.S. Cl. .......................................... 28/118; 28/119

(58) Field of Classification Search ................ 28/118, 28/119, 120, 121, 122, 116, 123; 604/385.17, 604/385.18, 385.21, 904; 264/402–405, 264/413, 479, 489, 103, 119, 123, 294, 320, 264/325, 327
See application file for complete search history.

(56) References Cited

U.S. PATENT DOCUMENTS

| | | | | |
|---|---|---|---|---|
| 1,997,467 A | * | 4/1935 | Manley | 433/136 |
| 2,425,004 A | * | 8/1947 | Rabell | 28/118 |
| 3,674,025 A | * | 7/1972 | Bleuer | 604/12 |
| 3,738,364 A | * | 6/1973 | Brien et al. | 604/375 |
| 4,027,673 A | * | 6/1977 | Poncy et al. | 604/369 |
| 4,081,884 A | * | 4/1978 | Johst et al. | 28/119 |
| 4,326,527 A | | 4/1982 | Wollangk et al. | |
| 4,591,523 A | | 5/1986 | Thompson | |
| 4,609,518 A | | 9/1986 | Curro et al. | |
| 4,629,643 A | | 12/1986 | Curro et al. | |
| 4,685,178 A | | 8/1987 | Nakanishi | |
| 4,839,216 A | | 6/1989 | Curro et al. | |
| 4,951,368 A | * | 8/1990 | Heinen | 28/118 |
| 5,153,971 A | | 10/1992 | Van Iten | |
| 5,592,725 A | | 1/1997 | Brinker | |
| 5,788,910 A | | 8/1998 | McNeilis et al. | |
| 5,832,576 A | * | 11/1998 | Leutwyler et al. | 28/118 |
| 5,891,081 A | * | 4/1999 | McNelis et al. | 604/14 |
| 5,958,321 A | | 9/1999 | Schoelling et al. | |
| 6,003,216 A | * | 12/1999 | Hull et al. | 28/119 |
| 6,156,021 A | | 12/2000 | Tojkander | |

(Continued)

FOREIGN PATENT DOCUMENTS

EP    0 422 660 B1    2/1994

(Continued)

*Primary Examiner*—Amy B. Vanatta
(74) *Attorney, Agent, or Firm*—James E. Oehlenschlager; Ingrid N. Hickman; David M. Weirich

(57) ABSTRACT

The present invention provides for a method for producing a shaped tampon. The method includes the following steps: providing a mold having an inner surface, an outer surface, a first end, a second end, and an opening located in said second end; providing a tampon pledget; transferring said tampon pledget through said opening into said second end of said mold using a transfer member resulting in a tampon mold; self-sustaining said shaped tampon wherein said shaped tampon has an undercut; and removing said shaped tampon from said tampon mold.

8 Claims, 11 Drawing Sheets

U.S. PATENT DOCUMENTS

| | | | |
|---|---|---|---|
| 6,180,051 B1 * | 1/2001 | Schoelling | 264/443 |
| 6,283,952 B1 * | 9/2001 | Child et al. | 604/540 |
| 6,740,070 B1 * | 5/2004 | Agyapong et al. | 604/385.18 |
| 6,889,409 B1 * | 5/2005 | Friese et al. | 28/118 |
| 2003/0176844 A1 * | 9/2003 | Randall et al. | 604/385.17 |
| 2003/0176845 A1 * | 9/2003 | Kollwitz et al. | 604/385.17 |

FOREIGN PATENT DOCUMENTS

WO     WO 00/37013 A1     6/2000

* cited by examiner

METHOD OF PRODUCING A SHAPED TAMPON

This appication claims the benefit of Provisional Application No. 60/365,669, filed Mar. 18, 2002.

FIELD OF THE INVENTION

This invention relates to a method for producing a shaped catamenial tampon.

BACKGROUND OF THE INVENTION

A wide variety of absorbent catamenial tampons have long been known in the art. Most commercially available tampons are substantially cylindrical in shape prior to use in order to facilitate vaginal insertion. It is well known that the vaginal canal is not smooth and linear, but rather is very contoured. Some digital tampons have tapered insertion ends to make insertion more comfortable. Others have flared withdrawal ends, presumably to provide a larger surface area for the user to push against during insertion. Nevertheless, the inventors of the present invention recognize that comfort and/or ease of the insertion of tampons is an important unmet consumer need. It is also important to have a tampon which is comfortable once inside the contoured vaginal canal. Additionally, it is desirable that the features rendering a tampon comfortable and/or easy to insert do not compromise, and alternatively even enhance the fluid acquisition capabilities of the tampon in use. Therefore, there is a need for new and improved comfortable shaped tampons. The shaped tampon aids in the insertion ease and/or comfort.

Accordingly, there is a need for a new and improved method of forming a shaped tampon. The present method has been developed which permits the tampon to have a curvature (or profile) that corresponds more closely to the curvature of the woman's vagina than a straight or parallel-sided tampon.

SUMMARY OF THE INVENTION

The present invention relates to a method of manufacturing a shaped tampon. The inventive method is characterized by the steps of: providing a mold having an inner surface, an outer surface, a first end, a second end, and an opening located in said second end; providing a tampon pledget; transferring said tampon pledget through said opening into said second end of said mold using a transfer member resulting in a tampon mold; self-sustaining said shaped tampon wherein said shaped tampon has an undercut; and removing said shaped tampon from said tampon mold.

The inventive method may also be characterized by the steps of: heating a first split cavity mold member and second split cavity mold member to provide a first heated split cavity mold member and a second heated split cavity mold member; combining the first heated split cavity mold member and the second heated split cavity mold member which results in a heated split cavity mold member having a first end and a second end wherein the second end has an opening; providing a tampon pledget; placing the tampon pledget into a compression jaw; actuating the compression jaw thereby compressing the tampon pledget into a high aspect ratio shape resulting in a compressed tampon pledget; transferring the compressed tampon pledget from an actuated jaw into the heated split cavity mold member using a compression member; heating the shaped tampon in the heated split cavity mold member until the shaped tampon is self-sustained; partially separating the first heated split cavity mold member from the second heated split cavity mold member; and removing the shaped tampon.

The inventive method may also be characterized by the steps of: providing a first split cavity mold member having a first inner surface and a first outer surface; providing a second split cavity mold member having a second inner surface and a second outer surface; facing the first inner surface of the first split cavity mold member next to the second inner surface of the second split cavity mold member which results in a split cavity mold having a first end, a second end, and an opening located in the second end; providing a tampon pledget; placing the tampon pledget in between the first split cavity mold member and the second split cavity mold member; closing the first split cavity mold member and the second split cavity mold member with the tampon pledget inside; opening the first split cavity mold member and the second split cavity mold member with the tampon pledget inside; and self-sustaining the shaped tampon.

This invention relates to catamenial tampons, and more particularly, to a method of producing shaped tampons. All documents cited are, in relevant part, incorporated herein by reference; the citation of any document is not to be construed as an admission that it is prior art with respect to the present invention.

BRIEF DESCRIPTION OF THE DRAWINGS

While the specification concludes with claims particularly pointing out and distinctly claiming the subject matter that is regarded as forming the present invention, it is believed that the invention will be better understood from the following description taken in conjunction with the accompanying drawings, in which:

DETAILED DESCRIPTION OF THE INVENTION

Figure 1:
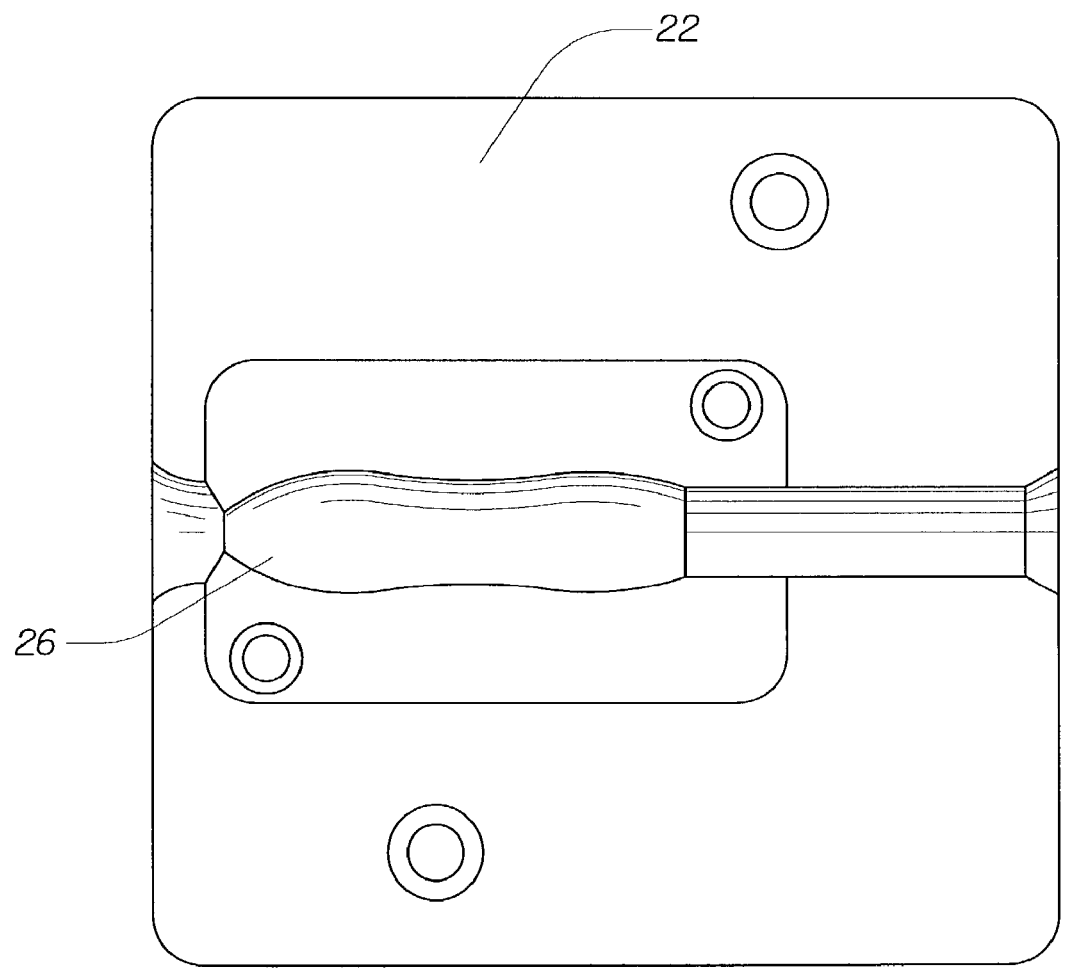
FIG. 1 is a top plan view of the first split cavity mold member.

The present invention provides a new and improved method of making a shaped tampon. The method has been developed which permits the tampon to have a curvature (or profile) that corresponds more closely to the curvature of the woman's vagina than a straight or parallel-sided tampon.

Section A will provide terms which will assist the reader in best understanding the features of the invention and not to introduce limitations in the terms not consistent with the context in which they are used in this specification. Theses definitions are not intended to be limiting. Section B is a detailed description of the drawings. Section C will discuss the different stages of the method of manufacturing a shaped tampon with an eye toward providing the greatest possible clarity. Section D will discuss the shaped tampon that results from the method of making a shaped tampon.

A. Terms

In general in this specification, the term "tampon" is used to refer to a finished tampon after the compression process referred to below. As used herein the term "tampon" refers to any type of absorbent structure that is inserted into the vaginal canal or other body cavities for the absorption of fluid therefrom. Typically, tampons are constructed from an absorbent material that has been compressed in one or more steps employing one or more parts of the absorbent material in the radial direction, axially along the longitudinal and lateral axes or in both the radial and axial directions to provide a tampon, which is of a size and stability to allow insertion within the vagina or other body cavity. A tampon that has been so compressed is referred to herein as a "self-sustaining" form. The term "self-sustaining" is defined below.

As used herein, "self-sustaining" is a measure of the degree or sufficiency to which the tampon retains the compression applied to the absorbent material of the tampon pledget such that in the subsequent absence of the external forces, the resulting tampon will tend to retain its general shape and size. For example, the resulting tampon's total volume growth subsequent to the removal of the external forces may be no greater than 200% of the external force-restrained shape, preferably less than 150% and even further preferred to not exceed 125% of the external force-restrained shape when observed at ambient room conditions of 73 degrees Fahrenheit temperature and 50% relative humidity. For tampons, it is found that control of the level of moisture within the tampon is a factor for helping the tampon to retain its shape subsequent the absence of the external compression forces. In one embodiment, the tampon is self-sustaining if the level of moisture is less than 10%. It will be understood by one of skill in the art that this self-sustaining form need not, and preferably does not persist during actual use of the tampon. That is, once the tampon is inserted and begins to acquire fluid, the tampon will begin to expand and may lose its self-sustaining form.

As used herein the terms "pledget" or "tampon pledget" are intended to be interchangeable and refer to a construction of absorbent material prior to the compression of such construction into a tampon as described above. Tampon pledgets are sometimes referred to as a tampon blank, or a softwind, or a pad, and the term "pledget" is intended to include such terms as well.

As used herein the terms "vaginal cavity," "within the vagina," and "vaginal interior," are intended to be synonymous and refer to the internal genitalia of the human female in the pudendal region of the body. The term "vaginal cavity" as used herein is intended to refer to the space located between the introitus of the vagina (sometimes referred to as the sphincter of the vagina) and the cervix and is not intended to include the interlabial space, including the floor of vestibule. The externally visible genitalia generally is not included within the term "vaginal cavity" as used herein. As used herein, "vaginally insertable shape" refers to the geometrical form of the absorbent tampon after compression. While not to be limited to such dimensions, a typical compressed tampon for human use is 10–16 millimeters wide and 40–50 millimeters long depending on absorbency. For other mammals, typical tampon dimensions may vary based on differences in vaginal cavity geometry. While the tampon may be compressed into a substantially cylindrical configuration, other shapes are possible. These may include shapes having a cross section or cross-section element that may be described as rectangular, triangular, trapezoidal, semi-circular, hourglass, or other suitable shapes.

As used herein "compressed" refers to pressing, compacting or squeezing together or to reduce in size or volume as if by squeezing. One method of compaction includes motion of flexible members actuated through air or hydraulics. The tampons herein are typically formed by laterally compacting or rolling the tampon pledget such that the formation processed result in a compressed structure in a vaginally insertable shape.

The term "folded" as used herein, is the configuration of the compressed absorbent member that is incidental or deliberate to compaction of the absorbent material. The folded configuration is characterized by at least one bend at least in a portion of the tampon pledget such that portion of the tampon pledget is positioned with a different plane than before with the observation that the surface regions near the bend are in a different distal and angular relationship to each other after the folding has taken place. In the case of the lateral compaction of a generally flat tampon pledget, there may exist one or more bends or folds of generally 180 degrees such that the surface regions on either side of the bend may be juxtaposed or even in co-facial contact with each other.

As used herein, "mold" is a structure intended for shaping a compressable or compactable (or fluent) material wherein the structure is so arranged as to define a space or cavity for retaining the compressible material and wherein the compressible material initially having a different form or no definite form conforms to the shape of the space or cavity by restraining force of the mold structure on the compressible material and preferably changes to a self-sustaining shape even after removal from the mold structure. As defined in this development, the mold cavity or space substantially or fully defines the full surface of the compressed tampon. The mold may have an ingress port or opening wherewith the tampon pledget is introduced into the mold cavity.

As used herein, "holds together" is when two objects are in a close association or relationship with one another and the two objects may be considered a whole.

As used herein, the tampon compression machine is a machine assembly that includes parts that may compress the tampon pledget. Typically a tampon pledget compressed in the tampon compression machine is then transferred to a mold for final shaping into a self-sustaining form of a vaginally insertable shape where often though not required, the mold further compresses parts of the tampon beyond that which the tampon compression machine accomplished prior.

As used herein, the V-Block of the tampon compression machine is used to compress a substantially flat tampon pledget.

As used herein, a transfer member is any member that can used to transfer a compressed tampon pledget.

As used herein, the compression member is any member that can be used to compress a tampon pledget. It can also function optionally as a transfer member.

As used herein, actuating is any force delivered by an electric motor, mechanical transmission, pneumatically, linear drive, manual, and/or hydraulic.

As used herein, a high aspect ratio shape is any shape in which the length is greater than the diameter or width of the shape. The shape may not necessarily contain any defined circles, arcs, or cross-sectional portions.

As used herein, the term "chevron-shaped" is a figure, pattern, or object having the shape of a "V", an inverted "V", broad "U", or an inverted "U."

As used herein, "facing" is to lie near, juxtaposed or in actual contact to another object where any part of a first object is near, juxtaposed or in actual contact with any part of another object.

As used herein, the inner surface of the split cavity mold member is that surface which contacts the material to mold the tampon. The inner surface is shaped or profiled to achieve the desired shape for the tampon. Though not to be limiting, the inner surface of the mold may be any shape as desired. An example of an inner surface with a concave portion is shown in FIG. 1.

Figure 4:
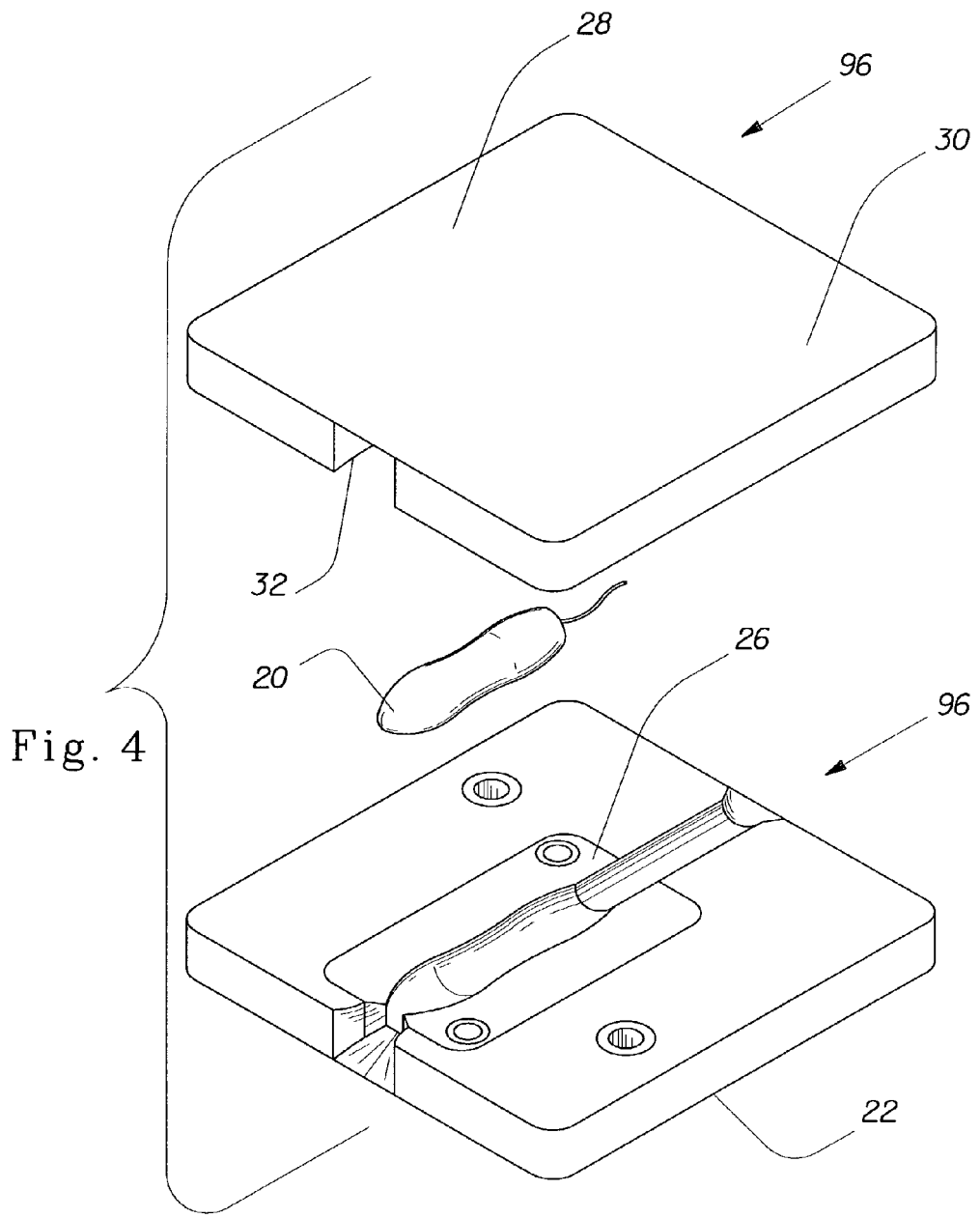
FIG. 4 is an exploded view of split cavity mold.

As used herein, the outer surface of the split half cavity mold is that surface external to the inner surface and can be profiled or shaped in any manner. Often the preferred outer surface shape is dictated by what form or shape is either most convenient to the manufacturer for smooth production and/or least cost. An example of the outer surface with a convex portion is shown in FIG. 4.

As used herein, the term "split cavity mold" is a mold comprised of two or more members that when brought together complete the inner surface of the mold, which is intended for shaping a compressable or compactable (or fluent) material wherein the complete mold structure is so arranged as to define a space or cavity. Each member of the mold comprises at least a portion of the inner surface that when brought together or closed complete the mold structure. The split cavity mold is designed such that at least two or more of the mold members can be at least partially separated, if not fully separated, preferably after the tampon has acquired a self-sustaining shape, to expand the cavity volume circumscribed by the inner surface(s) thus permitting the easier removal of the tampon from the mold. Partial separation can occur when only a portion of two mold members are separated while other portions of the two mold members remain in contact. Where each member's inner surface portion joins the inner surface portion of another member, those points of adjacency can define a line, a curve, or another seam of any convoluted intersection or seam of any regular or irregular form. For the purposes of this invention, there is at least one complete pathway (regardless of the tortuousness of the path(s)) that travels from along the entire length of the central portion of the tampon, and preferably extends to near the insertion end and/or the insertion tip 88 and/or the withdrawal end (i.e. base or bottom) 66 of the tampon.

The term "split half cavity" indicates a mold that comprises at least two major members. The term "half" indicates one of the two mold members that when brought together complete the mold structure. The term "half" does not necessarily mean that the members are substantially or exactly equivalent to each other in terms of dimensions, shape, volume, weight, etc.

Figure 3:
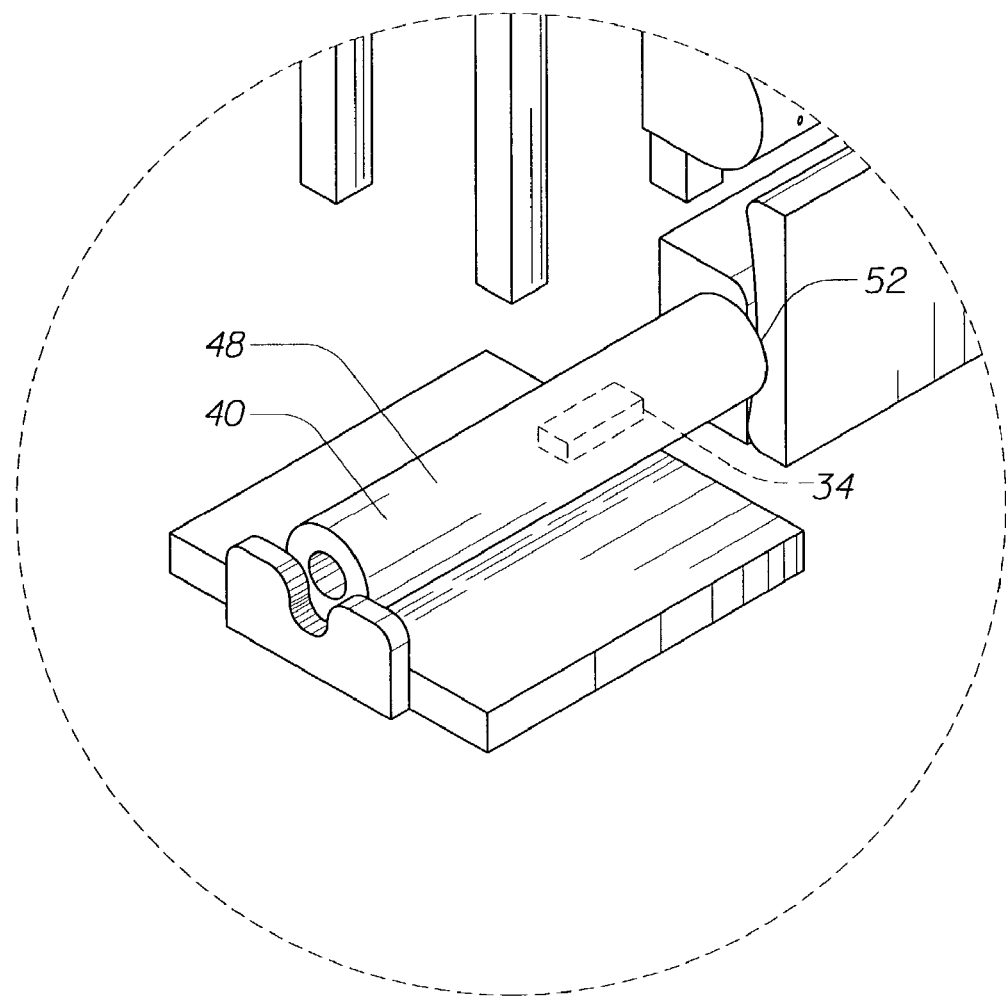
FIG. 3 is an enlarged perspective view of the joined sleeve cavity mold.
Figure 5:
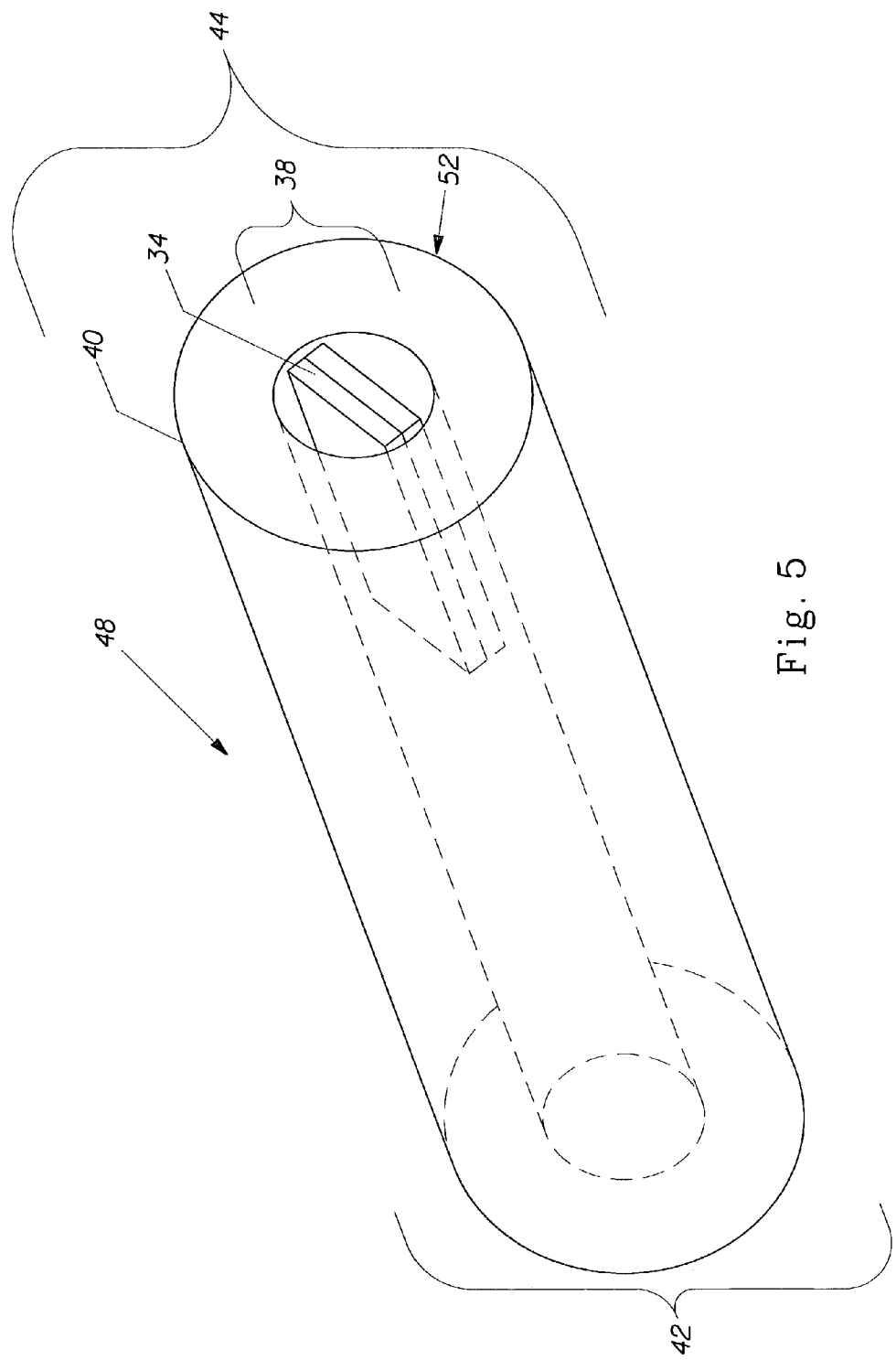
FIG. 5 is a perspective view of the split cavity mold inserted into an outer sleeve.

As used herein, an outer sleeve is an optional element. The outer sleeve partially surrounds the mold elements to preferably hold the mold elements in appropriate position relative to each other. The outer sleeve may be a carrying or transport member. The outer sleeve may be constructed from any suitable material including but not limited to tool steel, aluminum, or any form of polymer or resin suitable for a manufacturing envirormnent. While the outer sleeve 40 shown in FIG. 3 and FIG. 5 is generally cylindrical, other shapes such as triangular, semicircular, and rectangular shaped are also acceptable.

As used herein, a joined sleeve cavity mold comprises the outer sleeve and the split cavity mold.

As used herein, a tampon mold comprises a non-compressed or compressed tampon pledget and the split cavity mold.

A "linked split cavity mold member" is a split cavity mold member where at least two of the mold members are physically linked by a linking element or series of linking elements whereas at least one of the linking elements is movable in a linear and/or radial motion to thereby permit the two mold members to be repositioned in space relative to each other while maintaining linkage or connectiveness. The linking element(s) allow the two mold members to be repetitively, for example in a production cycle, be brought or held together (e.g. closed), then separated to the desired degree (e.g. partially opened) then returned to be brought or held together (e.g. closed). The linking elements can be of any form (e.g. bars, rods, linked cams, chains, cables, wires, wedges, screws, etc) and constructed of any material or combination of materials (e.g. tool steel, aluminum, wood, polymers, resins, etc) and actuated by any means including direct force transmission to the linking element(s) or force transmission via one or more of the mold members (or even the finished tampon itself during the opening cycle of the mold).

The term "heat setting" refers to the technique sometimes employed to help the tampon maintain a self-sustaining shape after compression. Heat setting is the introduction of heat energy by one means or another (e.g. thermal temperature gradient conduction, or microwave heating) relying on the present water molecules to disproportionately absorb the microwave energy to cause fiber (inter- or intra-fibrillar) bonding believed due to hydrogen bonding.

The "perimeter" of a segment of the tampon is a distance measured around the outer surface of the tampon perpendicular to the X axis. The perimeter may be measured, for instance, using Resin Embedded Microtome along with Scanning Electron Microscopy—S.E.M. (supplied by companies such as Resolution Sciences Corporation; Corte Madera, Calif.).

"Shaped tampons" refer to tampons having an undercut. The term "undercut" refers to tampons having a protuberance or indentation that impedes the withdrawal from a one piece mold. For example, shaped tampons created by the methods of the present invention may have at least one perimeter in the center of the tampon that is less than both an insertion end perimeter and a withdrawal end perimeter.

B. Detailed Description of the Drawings

FIG. 1 shows the first split cavity mold member 22 that has a first outer surface 24 (not shown) and a first inner surface 26. The present invention, however, is not limited to a structure having the particular configuration shown in the drawing. The first inner surface 26 comprises the desired shape of the resultant shaped tampon 20 (shown in FIG. 6). The shape of the resultant shaped tampon 20 is self-sustaining and may have an undercut 62 (shown in FIG. 6).

Figure 13:
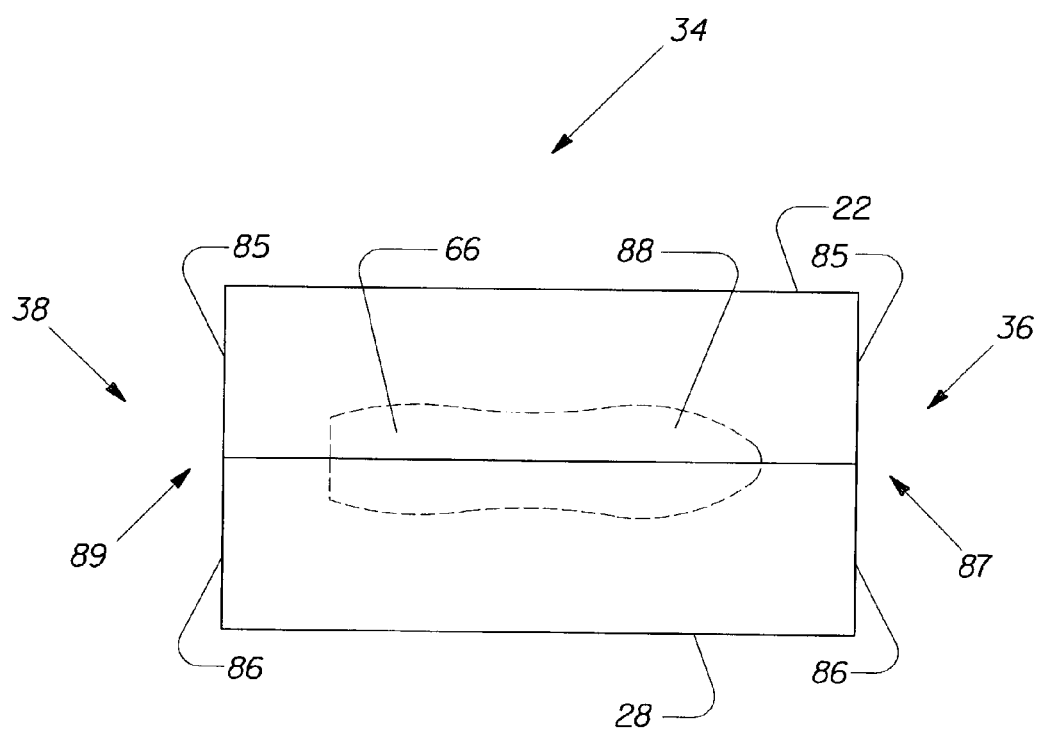
FIG. 13 is a side view of the split cavity mold.

As shown in FIG. 4 and FIG. 13, the second split cavity mold member 28 is substantially similar if not identical in size, shape, and dimension to the first split cavity mold member 22 and has a second outer surface 30 and second inner surface 32. As shown in FIG. 13, both the first split cavity mold 22 and second split cavity mold member 28 are combined to form a split cavity mold 34. The mold ends 85 of the first split cavity mold member 22 and the mold ends 86 of the second split cavity mold member 28 form the mold end 87 of the insertion end of the split cavity mold 34 and the withdrawal end 89 of the split cavity mold 34. The mole end 89 located at the withdrawal end 89 of the split cavity mold 34 is formed by the joining of the two split half cavity molds 22,28 where mold end 87 of the split cavity mold 34 in this example is fully closed and is used to form the tampon tip. The mold end 89 of the split cavity mold 34 is partially closed leaving an ingress port where the tampon pledget is introduced into the mold cavity.

Figure 2:
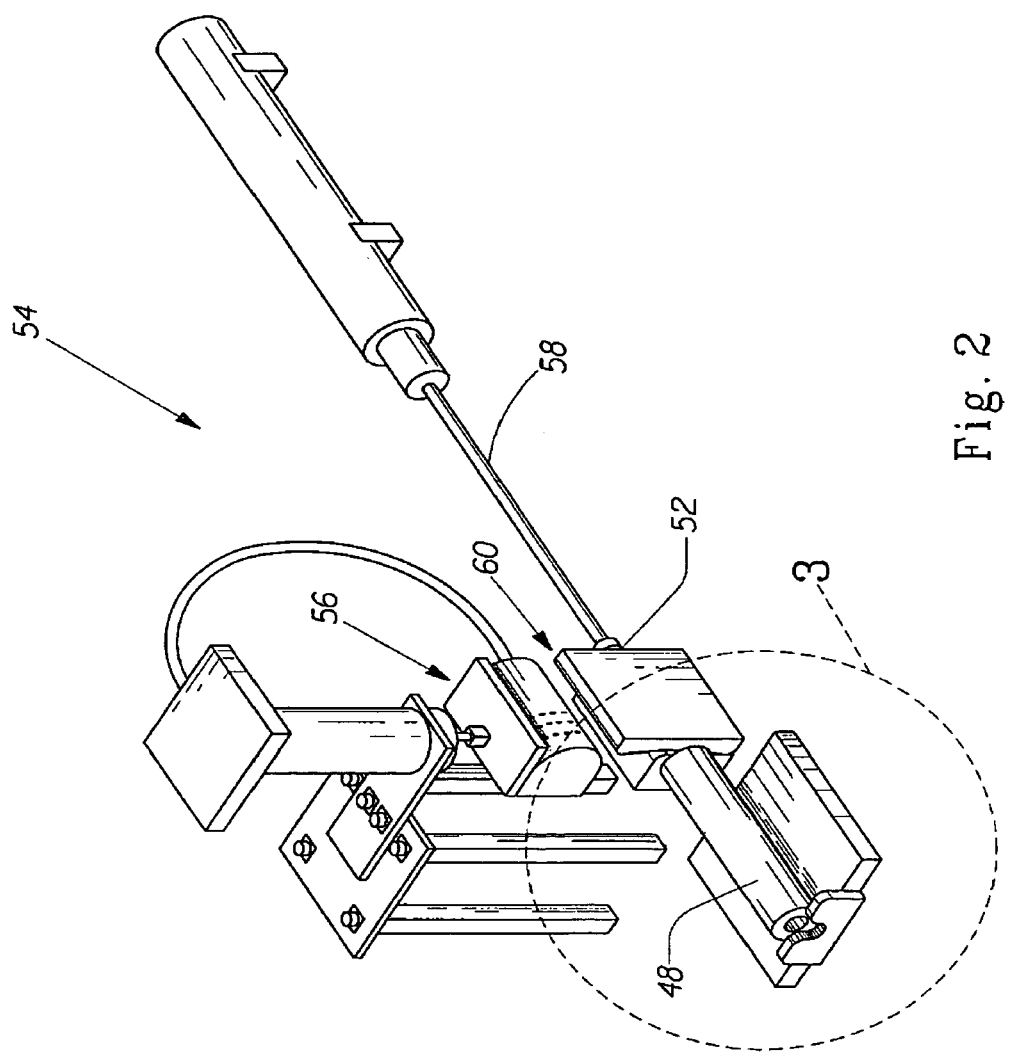
FIG. 2 is a perspective view of the tampon compression machine used in the process described.

FIG. 2 illustrates the embodiment of a machine for manufacturing a shaped tampon 20. FIG. 2 shows a diagram of the tampon compression machine 54. In one non-limiting embodiment, the tampon compression machine 54 may comprise a compression jaw 56, a compression rod 58, and a v-block holder 60. In the process of making a shaped tampon 20, a joined sleeve cavity mold 48, within which a split cavity mold (not shown) is held together, is placed into the v-block holder 60 of the tampon compression machine 54 with the transfer end 52 or ingress port facing the compression jaw 56 of the tampon compression machine 54. The joined sleeve cavity mold 48 is circled in FIG. 2. A tampon pledget 50 is placed into the compression jaw 56. The compression jaw 56 is actuated and compresses the tampon pledget 50 into a high aspect ratio shape tampon pledget 50. The high aspect ratio shape compressed tampon pledget 50 is transferred from the actuated compression jaw 56 into the joined sleeve cavity mold 48 by the compression rod 58. The joined sleeve cavity mold 48 is then removed from the compression machine 54. The resultant shaped tampon 20 is then removed from the joined sleeve cavity mold 48 and is self-sustained accordingly.

FIG. 3 shows an enlarged view of the joined sleeve cavity mold 48 in FIG. 2. The split cavity mold 34 is inserted into the outer sleeve 40 such that the second end 38 or ingress port of the split cavity mold is visible through the second end 44 of the outer sleeve 40. The outer sleeve 40 holds together the split cavity mold 34 to form a joined sleeve cavity mold 48 having a transfer end 52. The joined sleeve cavity mold 48 is placed on the v-block holder 60 of the tampon compression machine 54 so that the tampon pledget 50 can be transferred into the transfer end 52.

FIG. 4 shows an exploded view of the split cavity mold 34 with the resultant tampon 20 positioned between the first split cavity mold member 22 and the second split cavity mold member 28. The first split cavity mold member 22 and second split cavity mold member 28 are combined to form a split cavity mold 34 (as shown in FIG. 13). As shown in FIG. 4, in one non-limiting embodiment, the split half cavity molds are configured such that the first inner surface 26 and the second inner surface 32 face toward each other. These inner surfaces make up a cavity that is the desired shape of the shaped resultant tampon 20. As shown in FIG. 13, the split cavity mold 34 has a first end 36 and a second end 38 or ingress port.

FIG. 5 shows the split cavity mold 34 inserted into an outer sleeve 40. In the process described herein this particular example, the split cavity mold 34 will be inserted into an outer sleeve 40 with a first end 42 and a second end 44. The split cavity mold 34 is inserted into the outer sleeve 40 such that the second end 38 of the split cavity mold is visible through the second end 44 of the outer sleeve 40. The outer sleeve 40 holds together the split cavity mold 34 to form a joined sleeve cavity mold 48 having a transfer end 52.

Figure 6:
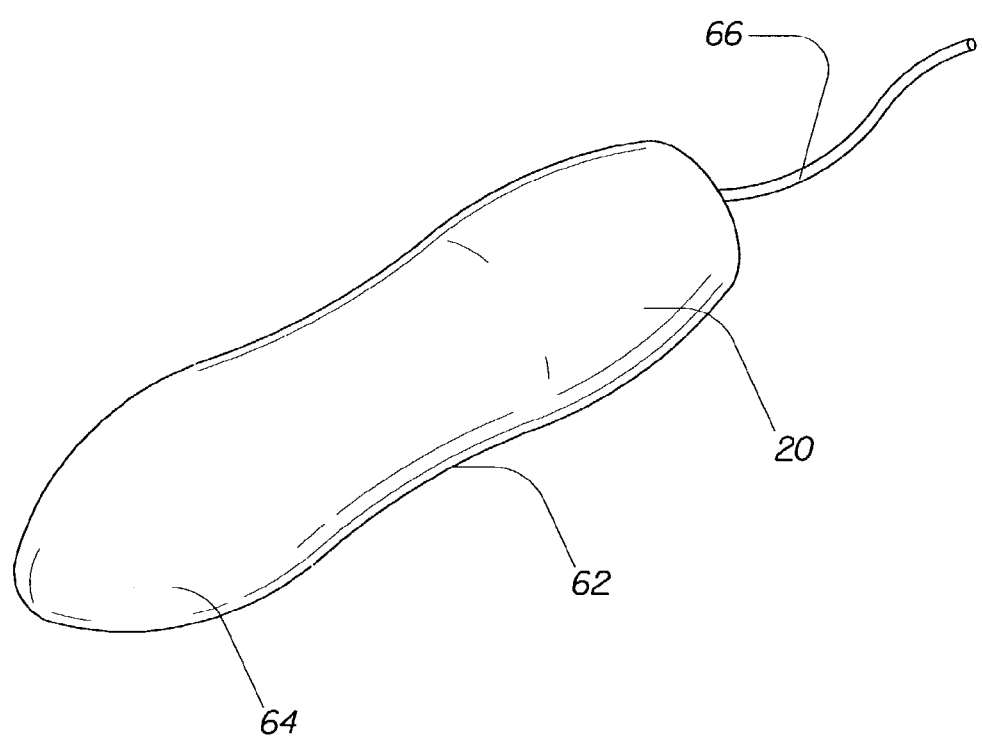
FIG. 6 is perspective view of the shaped tampon with an undercut.

FIG. 6 shows the shaped tampon 20 which may be produced from the method herein described and claimed. The tampon 20 produced has an undercut 62. The tampon 20 has an insertion end 64, a withdrawal end 66, and an undercut 62 that is located between the insertion end 64 and the withdrawal end 66.

C. Method

While previous tampons are manufactured in traditional molds using conventional methods, the shaped tampons require a specific new method of manufacturing. Meant to be illustrative but not limiting, below is a method of making a shaped tampon with discussion of other example variations in the method steps.

A first split cavity mold member 22 is provided. The first split cavity mold member 22 has a first inner surface 26 and a first outer surface 24. A second split cavity mold member 28 may be provided. If provided, the second split cavity mold member 28 has a second inner surface 32 and a second outer surface 30. Depending upon the choice of heat-setting technique, the mold may be constructed from a wide variety of materials commonly such as stainless steel or microwave transparent material.

The first inner surface 26 of the first split cavity mold member 22 is placed next to the second inner surface 32 of the second split cavity mold member 28. The combination of the first split cavity mold member 22 and the second split cavity mold member 28 results in a split cavity mold 34. The split cavity mold 34 has a first end 36 and a second end 38. The second end 38 of the split cavity mold 34 has an opening 96 or ingress port 96.

In an alternative embodiment, an outer sleeve 40 may be used to hold together the split cavity mold 34. The outer sleeve 40 has a first end 42 and a second end 44. The second end 44 has an opening.

If an outer sleeve 40 is used to accomplish holding together the split cavity mold 34, the following steps occur. The first end 36 of the split cavity mold 34 may be inserted first into the outer sleeve 40. The opening of the split cavity mold 34 is visible through the second end 44 of the outer sleeve 40. The combination of the split cavity mold 34 and the outer sleeve 40 forms a joined sleeve cavity mold 48 with a transfer end 52. Next, the joined sleeve cavity mold 48 is loaded into a v-block holder 60 of a tampon compression machine 54 with the transfer end 52 of the joined sleeve cavity mold 48 facing a compression jaw 56 in the tampon compression machine 54.

In an alternative embodiment, a linked split cavity mold member may be used to hold together the mold members. The advantage of a linked split cavity mold member is that the linkage can provide consistently repeatable positioning of the mold members relative to each other both during the partial open/open and close times of the molding cycle. This allows for high speed, and reliably repetitive production from one tampon to another.

Figure 12A:
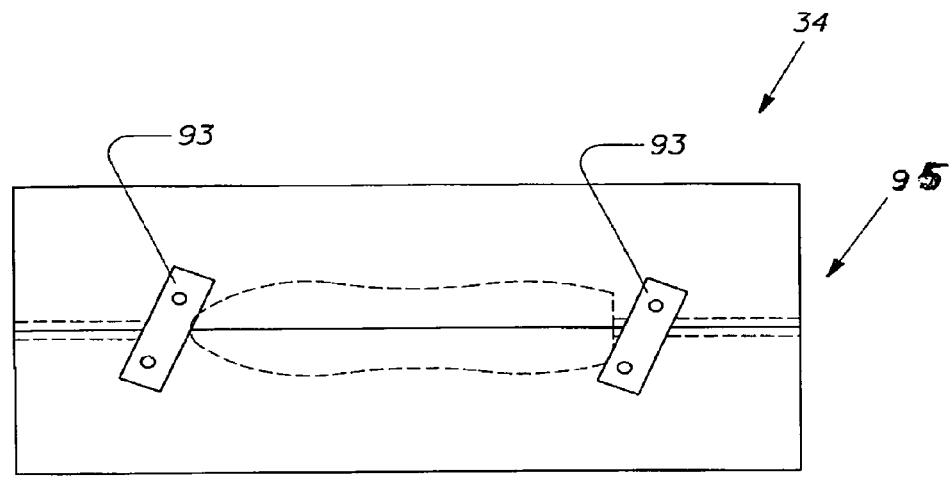
FIG. 12A is a side view of the pivot arm linked split cavity mold member.
Figure 12B:
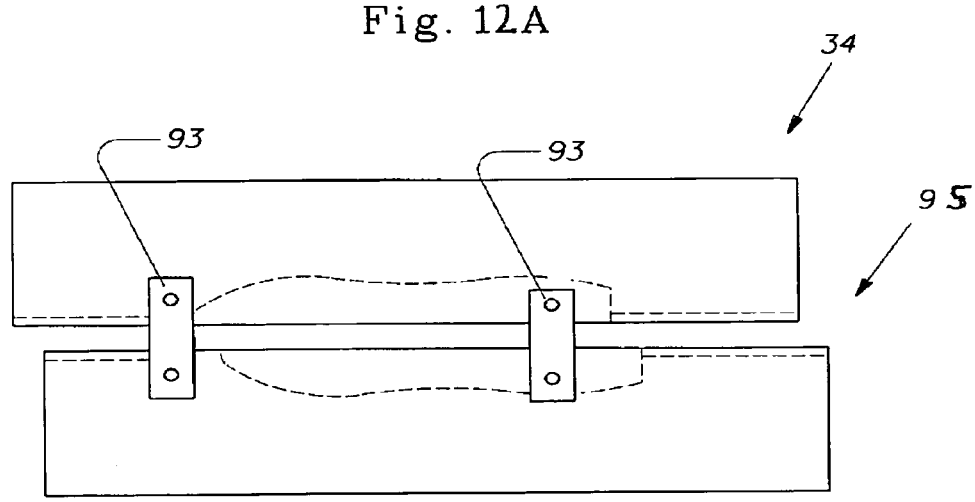
FIG. 12B is a side view of the pivot arm linked split cavity mold member.

FIG. 12A and FIG. 12B show a split cavity mold consisting of two halves defining a generally concave inner cavity with a generally rectilinear outer surface profile, depicts an alternate form of linkage comprising two pairs of pivot arms 93 with a pair on opposite sides of the mold. The pivot arms span across the two length-wise mold member seams. FIG. 12A shows one view of the closed combined mold cavity that is ready to accept a tampon pledget through the opening at end 95 or the ingress port. After the tampon is self-sustaining, the mold is opened manually, mechanically, and/or hydraulically to a degree of separation that allows removal of the tampon from the mold. Opening is accomplished by moving one mold member farther from the other while also shifting it toward one end. In this example, this orients the pivot arms away from the initial inclined position to a more normal direction thereby creating an opening or gap between the two mold members. As shown in FIG. 12B, as needed the mold can be held open during the tampon removal operation. The mold is then ready to be closed to accept another tampon pledget. When closed, the mold members (whether linked or not) can be locked by any known means including but not limited to interlocking surfaces or tabs as part of the mold itself, third element members that are first attached to the mold members and can lock with each other, etc. The mold separation and closure motion can be accomplished by any known means or drives with external mold elements provided to aid in force transmission as needed, including but not limited to moving arms, screws, wedges, chains, ropes, cams, pistons, lifters, rods, gears, etc.

Figure 11A:
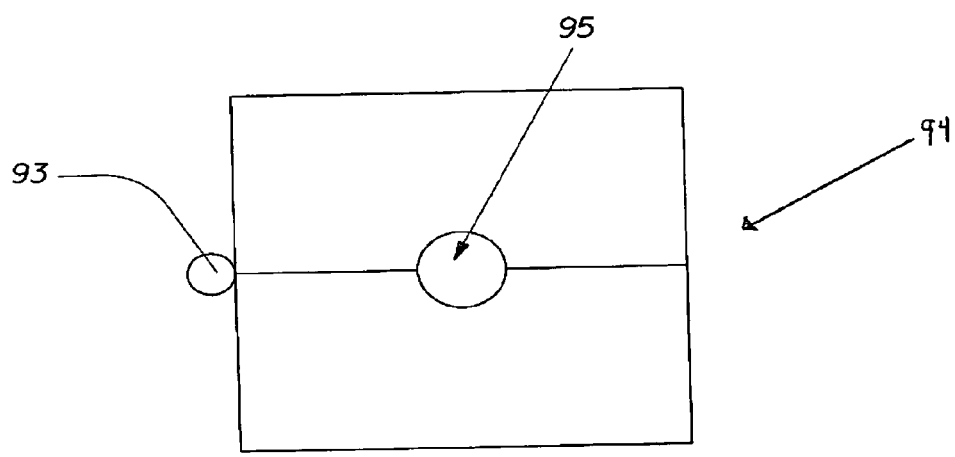
FIG. 11A is a perspective view of the hinged linked split cavity mold member.
Figure 11B:
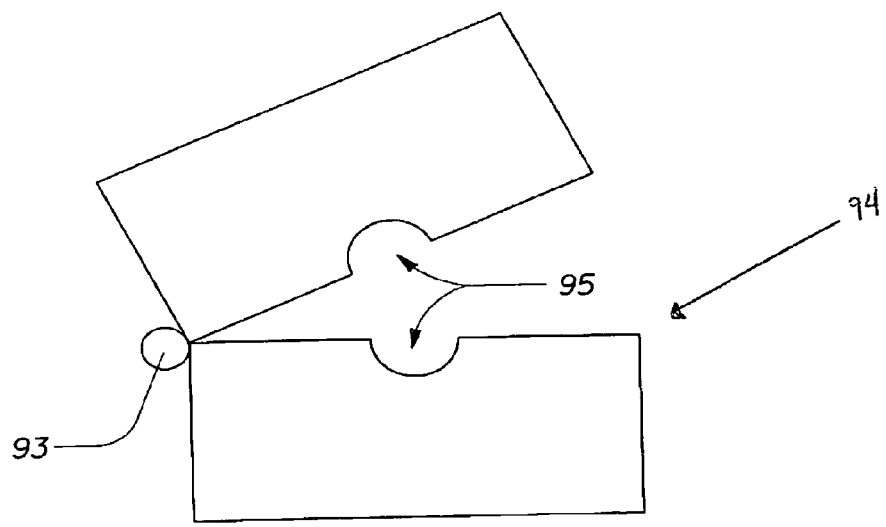
FIG. 11B is a perspective view of the hinged linked split cavity mold member.

Referring to FIGS. 11A and 11B, a split cavity mold consisting of two halves defining a generally concave inner cavity with a generally rectilinear outer surface profile. Along one of the mold seams is located a long hinge 93, for example a piano-type hinge. FIG. 11A shows two views of the closed combined mold cavity that is ready to accept a tampon pledget through the opening at end 95 or the ingress port. Referring to FIG. 11B, after the tampon is self-sustained, the mold is opened manually, mechanically, and/or hydraulically to a degree of separation that allows removal of the tampon from the mold by pivoting one member away from the other member through the hinge pivot motion. As needed the mold can be held open during the tampon removal operation. The mold is then ready to be closed to accept another tampon pledget. When closed, the mold members (whether linked or not) can be locked by any known means including but not limited to interlocking surfaces or tabs as part of the mold itself, third element members that are first attached to the mold members and can lock with each other, etc. The mold separation and closure motion can be accomplished by any known means or drives with external mold elements provided to aid in force transmission as needed, including but not limited to moving arms, screws, wedges, chains, ropes, cams, pistons, lifters, rods, gears, etc.

A tampon pledget is provided. The tampon 20 of the present invention may be formed from any suitable tampon pledget, such as tampon pledget 50 shown in FIG. 7. In an alternative embodiment the tampon pledget 50 may have a withdrawal means 89. If the embodiment includes a withdrawal means 89, the withdrawal means 89 is preferably removed out of the path of a jaw movement. The withdrawal means will be joined to the tampon and will be graspable for digital removal after use. The withdrawal means may be joined to any suitable location on the tampon. The withdrawal means may be attached in any suitable manner known in the art including looping, knotting, sewing, adhesive attachment, or a combination of known bonding methods. The withdrawal means may be integral with the absorbent material. Any of the withdrawal means currently known in the art may be used as a suitable withdrawal mechanism.

In addition, the withdrawal means can take on other forms such as a ribbon, loop, tab, or the like. The withdrawal means may be a tampon cord.

Figure 7:
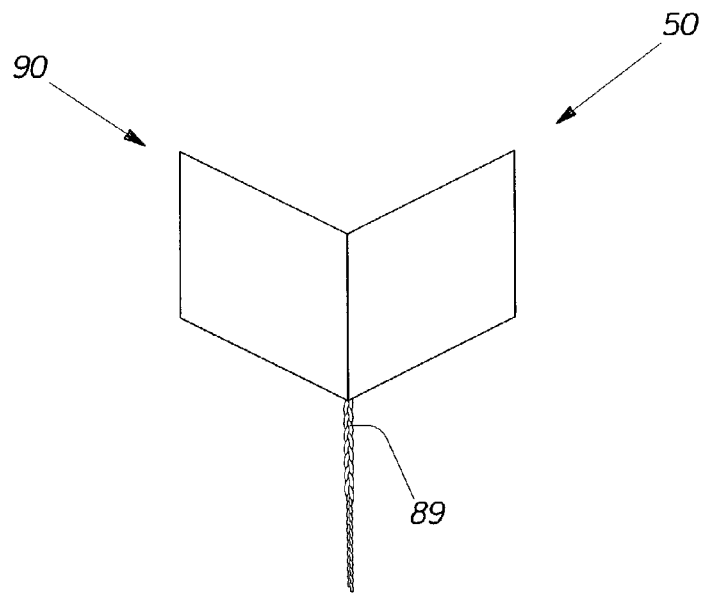
FIG. 7 is a perspective view of a tampon pledget from which a tampon of the present invention may be made by suitable compression.

The tampon pledget 50 portion of the tampon 20 which will be compressed to form the tampon 20 may be any suitable shape, size, material, or construction. In the embodiment shown in FIG. 7, tampon pledget 50 is a batt of absorbent material which is a generally "chevron shaped" pad 90 of absorbent material. While the pledget 50 shown in FIG. 7 is generally chevron shaped 90, other shapes such as trapezoidal, triangular, semi-circular, and rectangular shaped are also acceptable.

Figure 8:
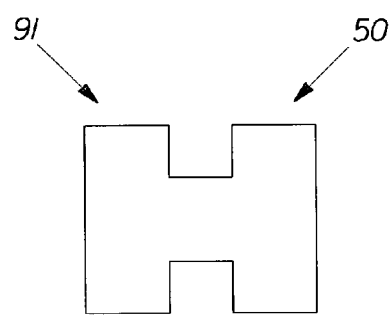
FIG. 8 is a perspective view of an alternative shape for a tampon pledget.
Figure 9:
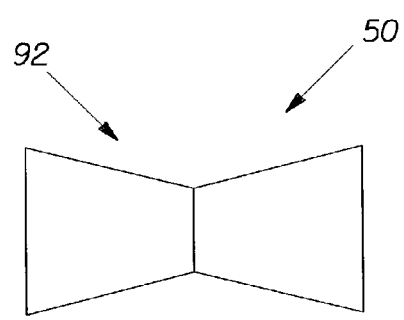
FIG. 9 is a perspective view of another alternative shape for a tampon pledget.

Other shapes that also tend to produce this variation are also possible. For example, the pledget may be generally "H" shaped 91, such as shown in FIG. 8. A "bow tie" shape 92 such as is shown in FIG. 9 is also suitable. While a chevron shaped pledget 50 is suitable, the edges of the chevron may be somewhat "rounded off" in order to facilitate high speed manufacturing operations. As an alternative to the shapes of pledgets described above, a tampon pledget 50 of the present invention may have a uniform shape such as a rectangular shape, but vary in absorbent material density or thickness along the axial extent of the pledget. A more detailed description of liquid-absorbing materials and pledget shapes and dimensions can be found in co-pending case Ser. No. 10/039,979, filed Oct. 24, 2001, entitled "Improved Protection and Comfort Tampon", to Agyapong et al.

A wide variety of absorbent catamenial tampons have long been known in the art. Most currently commercially available tampons are made from a tampon pledget that has been compressed into a substantially cylindrical form. Tampon pledgets of a variety of types and constructions have been described in the art. Prior to compression, the pledget may be rolled, spirally wound, folded, or assembled as a rectangular or laminar pad of absorbent material.

Figure 10:
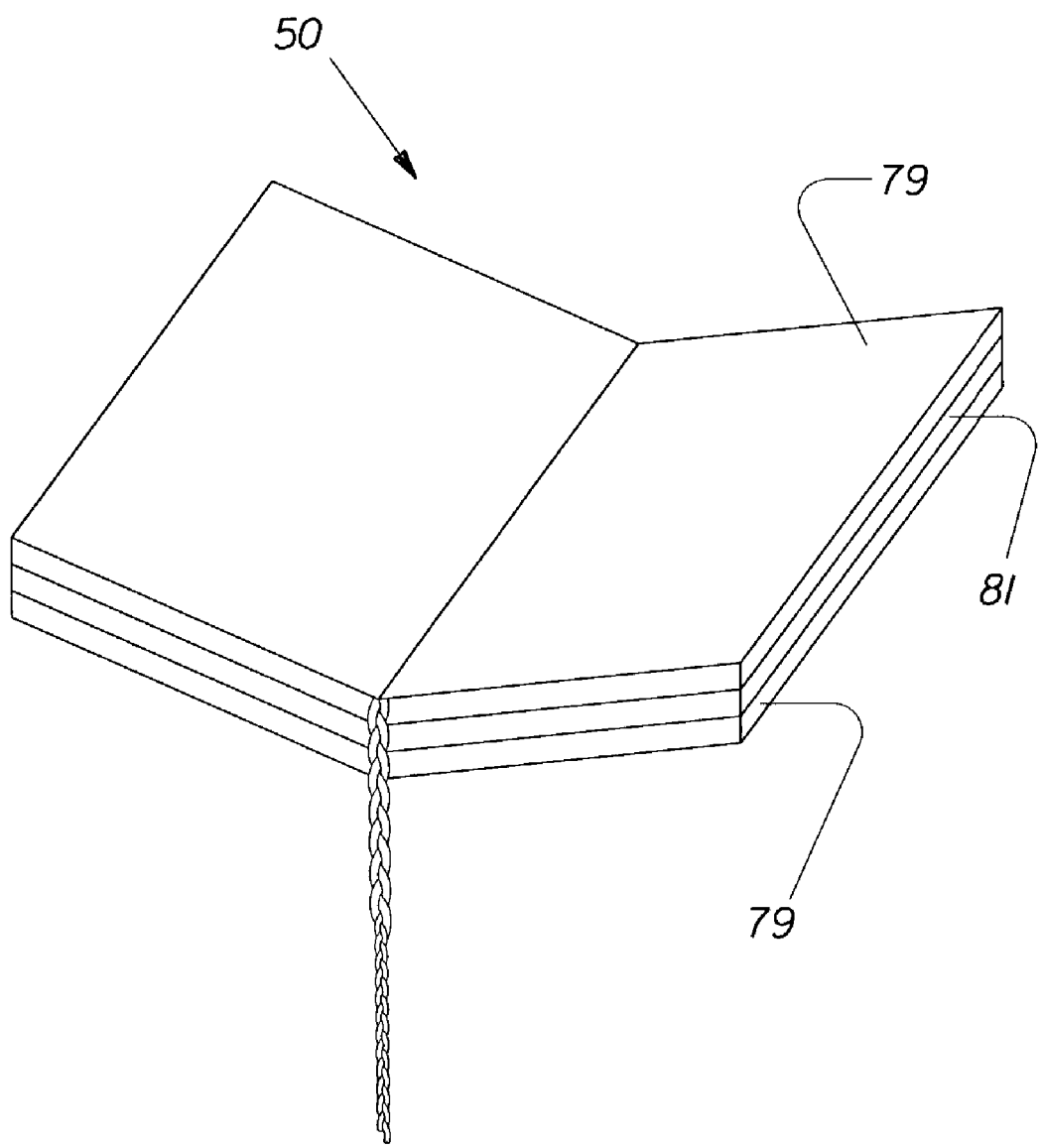
FIG. 10 is a perspective view of the tampon pledget shown in FIG. 7 that shows the layers of such pledget.

In preferred embodiments, the tampon pledget 50 may be a laminar structure comprised of integral or discrete layers. As is shown more clearly in FIG. 10, the tampon pledget 50 may comprise outer layers 79 and at least one intermediate layer 81 positioned between the outer layers 79. In other embodiments, the pad need not have a layered structure at all. The tampon pledget 50 may comprise a folded structure, may be rolled, may comprise a "petal" structure or any other of the structures, which are known in the art with respect to tampon pledgets.

The tampon pledget 50, and consequently, the resulting tampon 20 may be constructed from a wide variety of liquid-absorbing materials commonly used in absorbent articles such as rayon, cotton, or comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; foam; tissue including tissue wraps and tissue laminates; or any equivalent material or combinations of materials, or mixtures of these.

Preferred absorbent materials comprise cotton, rayon (including tri-lobal and conventional rayon fibers, and needle punched rayon), folded tissues, woven materials, nonwoven webs, synthetic and/or natural fibers. The tampon 20 and any component thereof may comprise a single material or a combination of materials. Additionally, superabsorbent materials, such as superabsorbent polymers or absorbent gelling materials may be incorporated into the tampon 20.

The tampon pledget 50 and resulting tampon 20 may be formed of a soft absorbent material such as rayon, cotton (including either long fiber cotton or cotton linters) or other suitable natural or synthetic fibers or sheeting. The materials for the tampon 20 can be formed into a fabric, web, or batt that is suitable for use in the tampon pledget 50 by any suitable process such as airlaying, carding, wetlaying, hydroentangling, or other known techniques.

The pledget may be constructed from a wide variety of liquid-absorbing materials commonly used in absorbent articles. Such materials include but are not limited to rayon (such as GALAXY Rayon (a tri-lobed rayon structure) available as 6140 Rayon; or SARILLE L rayon (a round fiber rayon), both available from Acordis Fibers Ltd., of Hollywall, England), cotton, folded tissues, woven materials, nonwoven webs, synthetic and/or natural fibers or sheeting, comminuted wood pulp which is generally referred to as airfelt, or combinations of these materials. Additionally, superabsorbent materials, such as superabsorbent polymers or absorbent gelling materials may be incorporated into the tampon.

The tampon pledget 50 is compressed to create a compressed tampon pledget. In an alternative embodiment, the compression can be accomplished by placing the tampon pledget 50 into a compression jaw 56. Next, the compression jaw 56 is actuated. Upon actuating the compression jaw 56, a tampon pledget 50 is compressed into a compressed tampon pledget having a high aspect ratio shape, though other shapes are possible. These may include shapes having a cross section or cross section elements that may be described as rectangular, triangular, trapezoidal, semi-circular, or other suitable shapes.

The compression can be done by any known means in the art. Though generally not preferred, the compression can be done manually such as with the human hand.

The compressed tampon pledget is transferred into the transfer end (or ingress port) of the split cavity mold 34 using a transfer member such as pusher rod which can optionally & preferably be used to axially compress the tampon in the mold. Levers, a multiplicity of small diameter rods radially and axially arranged, or bellows of rubber or other deformable plastic material may also be used as transfer members. Transferring the tampon pledget into the split cavity mold 34 shapes the tampon pledget. The compressed tampon pledget and the split cavity mold result in a tampon mold. The tampon mold may have a first end and a second end. The second end of the tampon mold may have an opening. In an alternative embodiment the transfer member is removed. One non-limiting embodiment of the compression members is a compression pusher rod. The compression rod may use a force as appropriate. For this example a force of 50–1000 lbf is suitable. Overall the function of transfer and axial compression need to be distinctly different though a single pusher rod that provides both functions is preferred. The transfer member can be a human finger, rod as mentioned before, etc. Pressures and temperatures suitable for compression are well known in the art. While a variety of techniques are known and acceptable for these purposes, a modified tampon compressor machine available from Toray Engineering Co., Ltd, Osaka, Japan is suitable.

The shaped tampon is self-sustained. Sometimes the tampon can become self-sustained under the pressures and constraints of the mold itself; however, it is often desired to add a heat-setting step and to preferably conduct that heat-setting step while the tampon is at least partially inside the mold. Heat setting is the introduction of heat energy by one means or another (e.g. thermal temperature gradient conduction, or microwave heating) relying on the present water molecules to disproportionately absorb the microwave energy to cause fiber (inter- or intra-fibrillar) bonding believed due to hydrogen bonding. For heat-setting, control of the internal moisture of the tampon (such as pre-humidifying or pre-drying to certain moisture levels) can be used to control the resulting self-sustaining behavior.

Heat-setting can be accomplished by microwaving, thermal conduction, ultrasonic-frequency heating, radio-frequency heating, electromagnetic energy input could be used such as radio waves, and infrared heating with infrared heat transparent molds. Section i. discusses the heat-setting method of microwaving. Section ii. discusses the heat-setting of thermal conduction method. Section iii. discusses the step of finished tampon removal.

i. Microwaving

If microwaving is used as a self-sustaining method, the tampon mold is placed in a microwaving unit where the mold and the outer sleeve (if used) are made form a microwavetransparent material(s). Next, microwave the tampon mold until the shaped tampon is self-sustained (i.e. properly heat-set). After the tampon is self-sustained, the shaped tampon 20 may be removed by removing the tampon mold from the microwaving unit. Next, if an outer sleeve is used, the split cavity mold 34 may be ejected from the outer sleeve 40 through the second end 44 of the outer sleeve 40. Then, the split cavity mold 34 is split, that is at least partially separated or separated to the desired degree (e.g. partially opened) to aid the next step of tampon removal. Finally, the shaped tampon 20 is removed from the split cavity mold 34.

ii. Thermal Conduction

If thermal conduction is used, first, a first split cavity mold member and a second split cavity mold member are heated where the mold and the outer sleeve (if used) are made from readily heat-conducting material(s). After the first split cavity mold member and a second split cavity mold member are heated, they are both termed heated split cavity mold member. In an non-limiting example, the molds may be heated to a temperature of 70–140 degrees Celsius.

The first heated split cavity mold member and the second heated split cavity mold member are combined which results in a heated split cavity mold member. Alternatively, the split cavity mold can be heated after combining. The heated split cavity mold member has a first end and a second end. The second end has an opening or ingress port.

A tampon pledget is provided. Alternatively for the thermal conduction technique, the molds can be heated after the tampon pledget has been introduced into the mold cavity.

The tampon pledget is placed into a compression jaw per above.

The compression jaw is actuated thereby compressing the tampon pledget into a high aspect ratio shape, though other shapes are possible. The compressed tampon pledget results in a compressed tampon pledget. These may include shapes having a cross section which may be described as rectangular, triangular, trapezoidal, semi-circular, or other suitable shapes.

The compressed tampon pledget is transferred from the actuated jaw into the heated split cavity mold member using a compression member. In an alternative embodiment the compression member is removed.

Conventional compression temperatures and pressures using standard equipment such as a tampon compressor machine available from Toray Engineering Co., Ltd, Osaka, Japan is suitable. Preferably, the direction of compression is primarily in the lateral direction as described above.

The shaped tampon 20 is heated in the heated split cavity mold member until the shaped tampon 20 is self-sustained.

The first heated split cavity mold member and the second heated split cavity mold member are split, that is at least partially separated or separated to the desired degree (e.g. partially opened) to aid the next step of tampon removal.

The shaped tampon 20 is removed. In an alternative embodiment the tampon pledget 50 may have a withdrawal means. If the embodiment includes a withdrawal means, the withdrawal means should be removed out of the path of a jaw movement.

iii. Finished Tampon Removal

Regardless of the preceding method steps, there are a variety of alternative ways to remove the finished tampon after the mold has been split, that is at least partially separated or separated to the desired degree (e.g. partially opened) to aid the next step of tampon removal. If the tampon has a withdrawal cord, the cord can be manually or mechanically grasped to pull, lift or draw the tampon from the mold or members of the mold. Alternatively, the tampon can be manually or mechanically grasped, hooked, picked, clamped, etc anywhere on the body and then pulled, lifted or drawn from the mold. A vacuum tool could also be used to adhere to the tampon body prior to withdrawal.

Alternatively, if the tampon stays juxtaposed to one or more mold member, that member could be oriented to encourage gravity to force the tampon to drop from the mold. A vibrational impact could be used to loosen the tampon from the mold member such as an impact, rap or ping applied singly or in series to the mold member body. Alternatively, the mold member or members could incorporate tampon ejection means such as an example of a knock-out or ejector pin(s) preferably with corresponding tight-fitting ejector pin hole(s), such as typical with injection molding techniques, where the pin pushes against the tampon body at the proper time to push the tampon body away from the inner surface. Another example of tampon ejection means incorporated into a mold member is to use ejector air through hole(s) or microporous hole(s) or pores where air pressure pushes against the tampon body at the proper time.

D. Description of Shaped Tapon

A tampon made by the present invention may optionally include a withdrawal cord, a secondary absorbent member, a liquid permeable overwrap material, and/or an applicator. The tampon pledget can be rectangular or any other shape prior to compression. A more detailed description of these features of tampons made by the method of the present invention can be found in co-pending case Ser. No. 10/039, 979, filed Oct. 24, 2001, entitled "Improved Protection and Comfort Tampon", to Agyapong et al.

While the method of the present invention can be useful in producing any size or shape tampon, the method of the present invention is particularly useful for producing tampons having at least one "waist" or "undercut" (narrowing point in the center region as compared to the withdrawal end and the insertion end), which can readily be seen, for example, in FIG. 6. More specifically, such "undercut" tampons include those which have at least a portion of the withdrawal end flared (increasing perimeter towards the withdrawal end) and at least one perimeter in the center region which is less than the largest insertion end perimeter. Tampons having this design are described in greater detail in co-pending case Ser. No. 60/365,672, filed Mar. 18, 2002, entitled "Shaped Tampon", to Kollwitz et al. Currently known methods of compressing and/or shaping tampons using one piece molds are typically not conducive to forming tampons having this type of undercut since they cannot easily be ejected from the mold given the undercut.

While particular embodiments of the present invention have been illustrated and described, it would be obvious to those skilled in the art that various other changes and modifications can be made without departing from the spirit and scope of the invention.

The invention claimed is:

1. A method of forming a shaped tampon which comprises the steps of:
   a. providing a mold having an inner surface, an outer surface, a first end, a second end, and an opening located in said second end, said inner surface having a profile correspondig to that of said shaped tampon;
   b. providing a tampon pledget;
   c. transferring said tampon pledget through said opening into said second end of said mold using a transfer member, wherein said tampon pledget and said mold result in a tampon mold;
   d. forming said tampon pledget into said shaped tampon, wherein said shaped tampon comprises an insertion end, a withdrawal end, and an undercut, wherein the insertion end is opposed to the withdrawal end and said undercut is located between the insertion end and the withdrawal end;
   e. self-sustaining said shaped tampon wherein said shaped tampon in its final desired shape has said undercut; and
   f. removing said shaped tampon from said tampon mold.

2. The method of claim 1 wherein said transfer member is a compression rod.

3. The method of claim 1 wherein said tampon pledget is compressed.

4. The method of claim 1 wherein said mold comprises a split cavity mold.

5. The method of claim 1 wherein the self-sustaining step is performed by:
   placing said tampon mold in a microwaving unit and microwaving said tampon mold until said shaped tampon is self-sustained.

6. The method of claim 1 wherein the step of forming said tampon pledget into said shaped tampon is performed by:
   placing said tampon pledget into a compression jaw and actuating said compression jaw thereby compressing said tampon pledget into a compressed tampon pledget having a high aspect ratio shape.

7. The method of claim 6 wherein said tampon pledget has a withdrawal means that is removed out of the path of said compression jaw during said step of forming said tampon pledget into said shaped tampon.

8. The method of claim 1 where after step c the following step occurs: removing said transfer member from said opening of said tampon mold.

* * * * *

UNITED STATES PATENT AND TRADEMARK OFFICE
CERTIFICATE OF CORRECTION

PATENT NO. : 7,047,608 B2
APPLICATION NO. : 10/150049
DATED : May 23, 2006
INVENTOR(S) : Sageser et al.

Page 1 of 1

It is certified that error appears in the above-identified patent and that said Letters Patent is hereby corrected as shown below:

Column 5, line 65, "tern" should read --term--.

Column 6, line 11, "envirormnent" should read --environment--.

Column 13, line 41, "Tapon" should read --Tampon--.

Column 14, line 20, "correspondig" should read --corresponding--.

Signed and Sealed this

Thirteenth Day of March, 2007

JON W. DUDAS
*Director of the United States Patent and Trademark Office*